US009939417B2

(12) United States Patent
McPeek

(10) Patent No.: US 9,939,417 B2
(45) Date of Patent: Apr. 10, 2018

(54) SYSTEMS AND METHODS FOR MONITORING AGRICULTURAL PRODUCTS

(71) Applicant: AGERpoint, Inc., New Smyrna Beach, FL (US)

(72) Inventor: K. Thomas McPeek, Orlando, FL (US)

(73) Assignee: AGERpoint, Inc., New Smyrna Beach, FL (US)

(*) Notice: Subject to any disclaimer, the term of this patent is extended or adjusted under 35 U.S.C. 154(b) by 552 days.

(21) Appl. No.: 13/907,147

(22) Filed: May 31, 2013

(65) Prior Publication Data

US 2013/0325346 A1     Dec. 5, 2013

Related U.S. Application Data

(60) Provisional application No. 61/654,312, filed on Jun. 1, 2012.

(51) Int. Cl.
| | |
|---|---|
| *G01N 33/00* | (2006.01) |
| *G01N 21/25* | (2006.01) |
| *G01B 5/00* | (2006.01) |
| *G01N 33/02* | (2006.01) |
| *G01N 21/17* | (2006.01) |
| *G01N 21/84* | (2006.01) |
| *G01B 11/24* | (2006.01) |

(52) U.S. Cl.
CPC ....... *G01N 33/0098* (2013.01); *G01B 5/0035* (2013.01); *G01N 21/251* (2013.01); *G01N 33/025* (2013.01); *G01B 11/24* (2013.01); *G01N 2021/1797* (2013.01); *G01N 2021/8466* (2013.01)

(58) Field of Classification Search
CPC ............ G01N 33/0098; G01N 21/251; G01N 33/025; G01N 2021/8466; G01N 2021/1797; G01B 5/0035; G01B 11/24
USPC ................................ 702/2; 356/4.01; 47/1.7
See application file for complete search history.

(56) References Cited

U.S. PATENT DOCUMENTS

| | | | | |
|---|---|---|---|---|
| 3,932,453 A | * | 1/1976 | Crovetti | C07D 231/16 548/372.1 |
| 5,845,229 A | * | 12/1998 | Rawlins | A01B 79/005 702/2 |
| 6,862,083 B1 | * | 3/2005 | McConnell, Sr. | A01B 79/005 356/4.01 |
| 7,112,806 B2 | * | 9/2006 | Lussier | G01N 21/6456 250/458.1 |
| 9,076,105 B2 | * | 7/2015 | Anderson | G06N 5/04 |
| 2003/0182259 A1 | * | 9/2003 | Pickett | A01B 79/005 |
| 2003/0182260 A1 | * | 9/2003 | Pickett | A01B 79/005 |
| 2007/0065857 A1 | * | 3/2007 | Glaser | G01N 21/314 435/6.11 |
| 2008/0074640 A1 | * | 3/2008 | Walsh | G01S 7/4818 356/5.01 |

(Continued)

OTHER PUBLICATIONS

Embree, Charles. "Effect of Blossom Density and Crop Load on Growth, Fruit Quality, and Return Bloom in Honeycrisp Apple". Hort Science 42 (7) pp. 1622-1625, 2007.*

(Continued)

*Primary Examiner* — Yoshihisa Ishizuka
(74) *Attorney, Agent, or Firm* — Bryan Cave LLP

(57) ABSTRACT

The present invention relates to systems and methods for monitoring agricultural products. In particular, the present invention relates to monitoring fruit production, plant growth, and plant vitality.

21 Claims, 5 Drawing Sheets

(56) References Cited

U.S. PATENT DOCUMENTS

| | | | | |
|---|---|---|---|---|
| 2010/0245344 | A1* | 9/2010 | Chen | G06T 19/00 345/419 |
| 2011/0022231 | A1* | 1/2011 | Walker | A01D 46/264 700/259 |
| 2011/0125477 | A1* | 5/2011 | Lightner | G05B 13/048 703/11 |
| 2012/0010789 | A1* | 1/2012 | Dulnigg | A01G 1/00 701/50 |
| 2012/0123681 | A1* | 5/2012 | Milori | G01N 21/6486 702/2 |
| 2014/0093138 | A1* | 4/2014 | Naganuma | G06K 9/00657 382/110 |
| 2015/0163992 | A1* | 6/2015 | Anderson | A01B 41/06 701/50 |
| 2015/0278719 | A1* | 10/2015 | Schueller | G06Q 50/02 705/7.11 |

OTHER PUBLICATIONS

Combined Tree Segmentation and Stem Detection Using Full Waveform LIDAR Data J. Reitberger a, *, P. Krzystek a, U. Stilla b a Dept. of Geoinformatics, Munich University of Applied Sciences, 80333 Munich, Germany (reitberger, krzystek)@fhm.edu b Photogrammetry and Remote Sensing, Technische Universitaet Muenchen, 80290 Munich, Germany., Jan. 2007.*

J. Reitberger, et al., 3D Segmentation of single trees exploiting full waveform LIDAR data, Journal article, published online May 17, 2009, Retrieved from the Internet: https://www.researchgate.net/publication/230642359.

Richard Lucas et al., Advances in forest Characterization, mapping and monitoring through integration of LiDAR and other remote sending datasets, Journal article, published Sep. 2008, SilviLaser, Edinburgh, U.K.

Clement Mallet et al., Full-waveform topographic lidar—State-of-the-art, Journal article, published Jan. 2009, Saint-Mandé Cedex, France.

Ricardo Sanz-Cartiella et al., Innovative LIDAR 3D Dynamic Measurement System to Estimate Fruit-Tree Leaf Area, Journal article, published online May 27, 2011. Retrieved from the Internet: http://www.mdpi.com/joumal/sensors.

* cited by examiner

Figure 2

| | | |
|---|---|---|
| TASK TYPE 1 | Determine diameter and/or circumference of the trunk of each tree<br>Determine the overall height of each tree<br>Determine the overall volume of each tree<br>Determine the leaf density of each tree<br>Determine average leaf color of each tree | TOOL 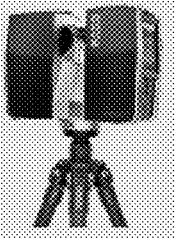 |
| TASK TYPE 2 | Determine the GPS location of each tree<br>Attach a unique RFID - Barcode identifier to each tree | TOOL  |
| TASK TYPE 3 | Determine the predicted yield from blossom and fruit | TOOL 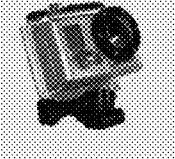 |
| TASK TYPE 4 | Seamlessly connect to existing industry standard software solutions for tracking grove operations and harvest control | TOOL 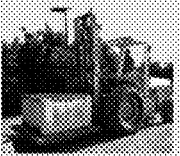 |

SYSTEMS AND METHODS FOR MONITORING AGRICULTURAL PRODUCTS

CROSS REFERENCE TO RELATED APPLICATIONS

This application claims priority to U.S. Provisional Patent Application No. 61/654,312, filed Jun. 1, 2012, which is herein incorporated by reference in its entirety.

FIELD OF THE INVENTION

The present invention relates to systems and methods for monitoring agricultural products. In particular, the present invention relates to monitoring fruit production, plant growth, and plant vitality.

BACKGROUND OF THE INVENTION

Accurate and timely machine counting of fruit on the tree or vine has long been considered impossible or impractical. Current methods rely on manual estimation and are often inaccurate and labor intensive. Inaccurate estimates lead to inaccurate crop forecasts and complicate pricing and grower's ability to forecast and plan.

What is needed is an improved method for accurately forecasting crop size and quality.

SUMMARY OF THE INVENTION

The present invention relates to systems and methods for monitoring agricultural products. In particular, the present invention relates to monitoring fruit production, plant growth, and plant vitality.

Embodiments of the present disclosure provide systems and methods for improved fruit tree analysis and crop predictions. The systems and methods described herein improve on the accuracy and efficiency of existing methods. The systems and methods of embodiments of the present invention find use in research and commercial agriculture, among other uses.

For example, in some embodiments, the present invention provides an analysis system, comprising: a) a data acquisition component; b) optionally, a transport component configured to transport the data acquisition component to collect data on fruit trees or vines; and c) a software component configured to analyze the data to generate analyzed data. In some embodiments, the data acquisition component comprises one or more devices selected from, for example, one or more of a 3D laser scanner, a survey grade GPS, thermal imaging, radio, sound and magnetic waves, a thermal imaging camera, multispectral and/or hyperspectral sensors, or a high speed high density (HD) video camera. In some embodiments, the data, for example, one or more of tree trunk diameter, height of tree, volume of tree, leaf density of tree, color of leaves on tree, GPS location of tree, bar code data for tree, number of blossoms on tree, presence of disease on said fruit or tree, subspecies of said tree, or an annotated or un-annotated photograph of said tree. The present invention is not limited to the analysis of a particular fruit tree or vine. Examples include but are not limited to, abiu, acerola, almond, amla (indian gooseberry), apple, apricot, aprium, avocados, bael, bananas, ber (indian plum), blackberries, blood orange, blueberries, breadfruit, calamondin, cantaloupe melon, carambola (starfruit), cashew, the fruit, cherries, chestnut, chocolate, chokecherry, citron, coconuts, coffee, corn plant, crabapple, cumaquat, currant, custard-apple, dates, dewberries, dragon fruit, durian, feijoa, fig, grapefruit, grapes, guava, hazelnut, honeydew, hops, jaboticaba, jackfruit, jujube, kaffir lime, key lime, kiwifruit, kumquat, lemons, limes, loganberries, longan, loquat, lychee, mandarin, mangoes, mangosteen, medlar, morello cherry, mulberries, natal plum, nectarines, olives, oranges, papayas, passion fruit, pawpaw, peaches, pears, pecan, persimmon, pineapples, plums, pluot, pomegranate, pomelo, prune, pummel, pumpkin, raspberries, red banana, rock melon, sabine, sapodilla (chikoo), sapote, soursop, starfruit, stone fruit, strawberries, strawberry tree, sugar-apple (sharifa), surinam cherry, tamarillo, tamarind, tangelos, tangerines, tomatoes, ugli, uglifruit/uniqfruit, walnut, watermelon, a grape vine, a tomato vine, a corn plant or an apple tree. In some embodiments, the software component further comprises a computer processor and a user interface configured to provide or display the analyzed data (e.g., to a user). In some embodiments, the analyzed data is, for example, one or more of tree health, predicted fruit yield, or predicted fruit ripening period.

In further embodiments, the present invention provides a method, comprising: a) collecting data on plants (e.g., fruit trees) using a data acquisition component transported by a transport component; and b) analyzing the data with a software component to generate analyzed data. In some embodiments, the method further comprises the step of using the analyzed data to guide fruit tree sprayers (e.g., to determine when to spray, how long to spray, and what chemicals to spray). In some embodiments, the method further comprises the step of identifying species and/or subspecies of the tree. In some embodiments, the method further comprises the step of identifying disease in the tree and/or fruit.

Additional embodiments are described herein.

DESCRIPTION OF THE FIGURES

FIG. 2 shows a task-methodology breakdown of systems and methods of embodiments of the present invention.

DEFINITIONS

Figure 1:
FIG. 1 shows an image of annotations of trees generated by systems and methods of embodiments of the present invention.
Figure 3:
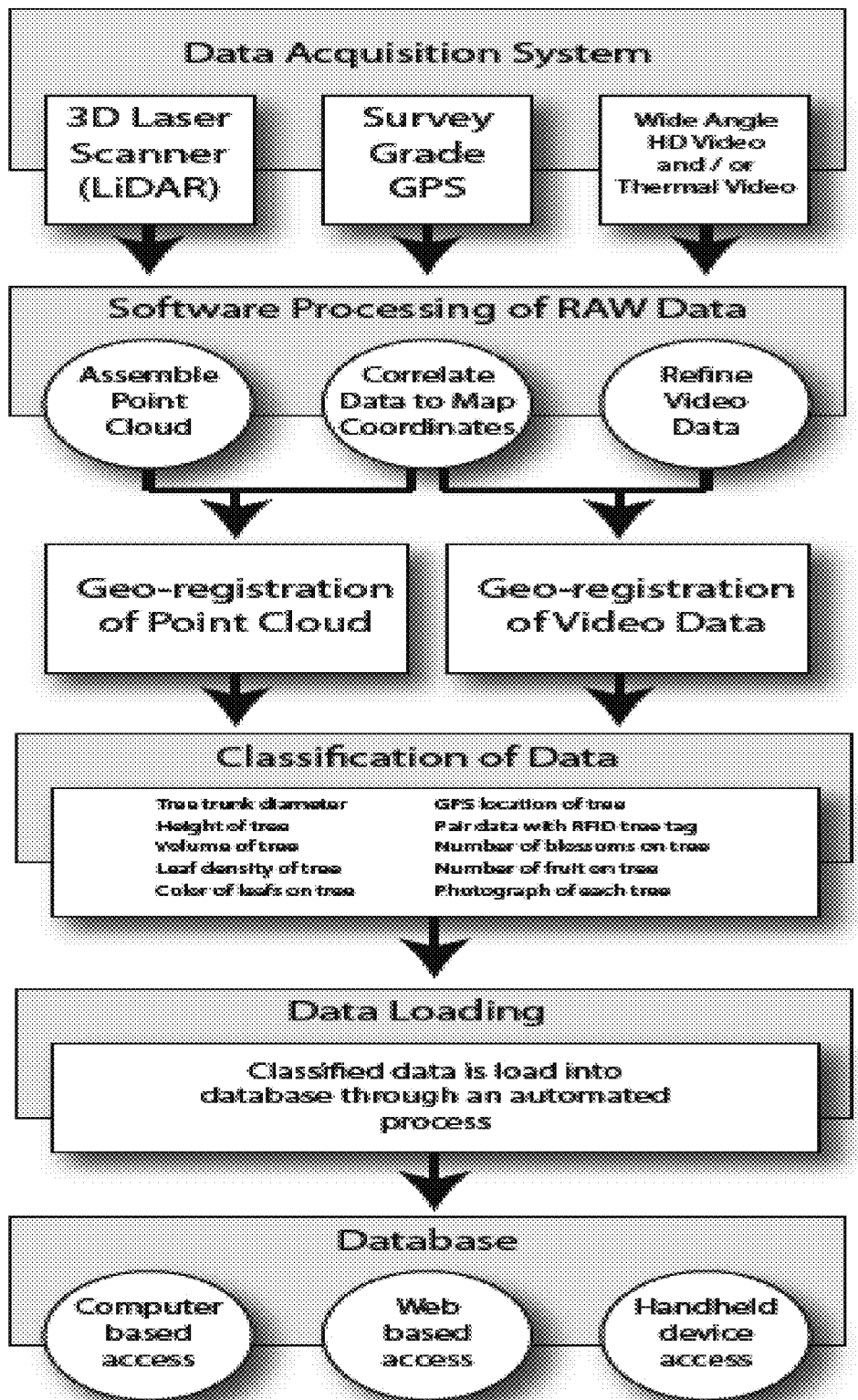
FIG. 3 shows a schematic of an exemplary crop analysis system for fruit bearing trees and vine crops.
Figure 4:
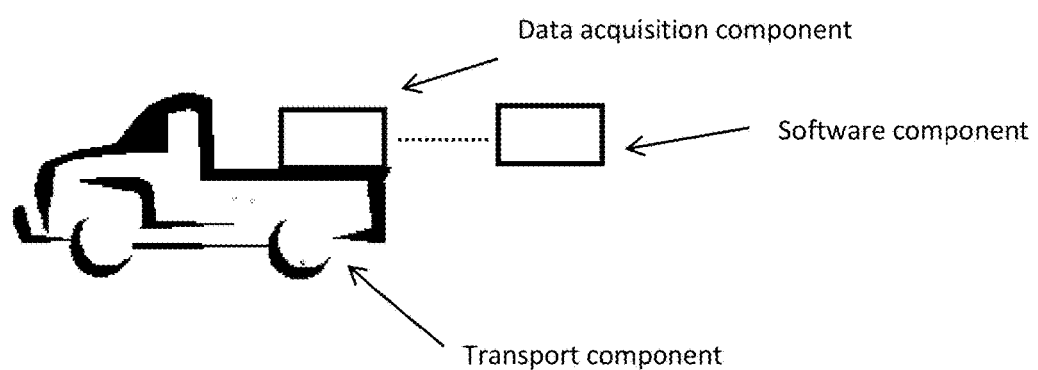
FIG. 4 shows a schematic of an exemplary crop analysis system for fruit bearing trees and vine crops.

To facilitate understanding of the invention, a number of terms are defined below.

As used herein, the terms "processor" and "central processing unit" or "CPU" are used interchangeably and refer to a device that is able to read a program from a computer memory (e.g., ROM or other computer memory) and perform a set of steps according to the program.

As used herein, the terms "computer memory" and "computer memory device" refer to any storage media readable by a computer processor. Examples of computer memory include, but are not limited to, RAM, ROM, computer chips, digital video discs (DVD), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the term "in electronic communication" refers to electrical devices (e.g., computers, processors, etc.) that are configured to communicate with one another through direct or indirect signaling.

As used herein, the term "survey grade GPS" refers to global positioning satellite (GPS) receivers that are able to map locations with a very high degree of accuracy. For example, in some embodiments, survey grade GPS receivers are accurate below 1 centimeter (0.4 inches) or lower.

As used herein, the term "fruit tree" refers to any woody tree or vine that produces a fruit. The term "fruit" refers to a part of a flowering plant that derives from specific tissues of the flower and is not limited to culinary fruits. Examples include but are not limited to, abiu, acerola, almond, amla (indian gooseberry), apple, apricot, aprium, avocados, bael, bananas, ber (indian plum), blackberries, blood orange, blueberries, breadfruit, calamondin, cantaloupe melon, carambola (starfruit), cashew, the fruit, cherries, chestnut, chocolate, chokecherry, citron, coconuts, coffee, corn plant, crabapple, cumaquat, currant, custard-apple, dates, dewberries, dragon fruit, durian, feijoa, fig, grapefruit, grapes, guava, hazelnut, honeydew, hops, jaboticaba, jackfruit, jujube, kaffir lime, key lime, kiwifruit, kumquat, lemons, limes, loganberries, longan, loquat, lychee, mandarin, mangoes, mangosteen, medlar, morello cherry, mulberries, natal plum, nectarines, olives, oranges, papayas, passion fruit, pawpaw, peaches, pears, pecan, persimmon, pineapples, plums, pluot, pomegranate, pomelo, prune, pummel, pumpkin, raspberries, red banana, rock melon, sabine, sapodilla (chikoo), sapote, soursop, starfruit, stone fruit, strawberries, strawberry tree, sugar-apple (sharifa), surinam cherry, tamarillo, tamarind, tangelos, tangerines, tomatoes, ugli, uglifruit/uniqfruit, walnut, watermelon, a grape vine, a tomato vine, a corn plant or an apple tree. In some embodiments, the fruit tree is a citrus tree (e.g., those described above).

DETAILED DESCRIPTION OF THE INVENTION

The present invention relates to systems and methods for monitoring agricultural products. In particular, the present invention relates to monitoring fruit production and plant growth.

The ability to accurately predict fruit yield and quality in advance of harvest provides a significant advancement in the fruit growing industry. The systems and methods of embodiments of the present invention provide an accurate inventory of crop holdings, including images and geo-location of each plant, as well as providing point cloud data dissemination.

Embodiments of the present invention provide systems and methods for assessing agricultural crops (e.g., fruit trees or vines). The systems and methods described herein find use in a variety of applications (e.g., providing information to companies engaged in growing fruit crops, those insuring fruit crops and those who invest in agricultural commodities).

The present invention is not limited to a particular fruit tree or vine. Any fruit bearing plant may be analyzed using the systems and methods described herein. Examples include but are not limited to abiu, acerola, almond, amla (indian gooseberry), apple, apricot, aprium, avocados, bael, bananas, ber (indian plum), blackberries, blood orange, blueberries, breadfruit, calamondin, cantaloupe melon, carambola (starfruit), cashew, the fruit, cherries, chestnut, chocolate, chokecherry, citron, coconuts, coffee, corn plant, crabapple, cumaquat, currant, custard-apple, dates, dewberries, dragon fruit, durian, feijoa, fig, grapefruit, grapes, guava, hazelnut, honeydew, hops, jaboticaba, jackfruit, jujube, kaffir lime, key lime, kiwifruit, kumquat, lemons, limes, loganberries, longan, loquat, lychee, mandarin, mangoes, mangosteen, medlar, morello cherry, mulberries, natal plum, nectarines, olives, oranges, papayas, passion fruit, pawpaw, peaches, pears, pecan, persimmon, pineapples, plums, pluot, pomegranate, pomelo, prune, pummel, pumpkin, raspberries, red banana, rock melon, sabine, sapodilla (chikoo), sapote, soursop, starfruit, stone fruit, strawberries, strawberry tree, sugar-apple (sharifa), surinam cherry, tamarillo, tamarind, tangelos, tangerines, tomatoes, ugli, uglifruit/uniqfruit, walnut, watermelon, a grape vine, a tomato vine, a corn plant or an apple tree. In some embodiments, the fruit tree is a citrus tree (e.g., those described above).

In some embodiments, the present invention provides systems and methods for a) determining the diameter and/or circumference of a tree trunk or vine stem, determining the overall height of each tree or vine, determining the overall volume of each tree or vine, determining the leaf density and average leaf color of each tree or vine; b) determining the GPS location of each plant and attaches a unique identifier (e.g., RFID (e.g., barcode identifier)) to each plant or vine; c) determining the predicted yield from identified blossom and fruit; and d) providing yield and harvest date predictions or other information to end users using a user interface. In some embodiments, the technology is used to size fruit while it is still on the tree (e.g., for applications where selective harvest is done based on size).

Embodiments of the present invention provide a variety of hardware and software systems to perform the described methods. In some embodiments, systems comprise one or more (e.g., all) the following components: survey grade GPS, 3D laser scanners, static and motion imaging (e.g., RGB, multi-spectral, hyper-spectral, NWIR and SWIR), high speed HD video, transport vehicles, computer software, computer processors, and user interfaces.

The global positioning system (GPS) is a space-based satellite navigation system that provides location and time information in all weather, anywhere on or near the Earth, where there is an unobstructed line of sight to four or more GPS satellites. GPS systems generally fall in one of four categories of accuracy, sub centimeter (0.39370 inch), sub decimeter (3.937 inches), sub meter (39.37 inches), and sub decameter (32.8 Feet). In some embodiments, survey grade GPS (e.g., sub centimeter) is used to locate fruit, and trees or vines to high levels of detail. Survey grade GPS receivers determine location to very high accuracy (e.g., 1 inch or less, 1 centimeter or less, etc.).

In some embodiments, commercially available equipment is utilized. For example, survey grade GPS receivers are available from a variety of suppliers (e.g., Igage Mapping Corporation, Salt Lake City, Utah; Hemisphere Inc., Calgary, Alberta, Canada; Trimble Navigation Limited, Sunnyvale, Calif.).

Figure 5:
FIG. 5 shows an example of a point cloud map of a fruit tree.

In some embodiments, 3D laser scanners are utilized to map fruit or tree or vine properties. 3D scanner is a colloquial term used to describe a device used for light detection and ranging (LiDAR) which is an optical remote sensing technology that can measure the distance to, or other properties of a target by illuminating the target with light. LiDAR can be found in two common forms direct energy detection, also known as incoherent, and coherent detection. Coherent systems are typically preferred for measurement systems. Both systems are currently available in two pulse formats:

micropulse and high-energy systems. The micropulse systems are eyesafe and require less energy to operate but this comes at the expense of higher computational post-processing requirements. LiDAR systems currently in use are capable of collecting nearly one million points per second. The data collected is represented as a point cloud as demonstrated in FIG. 5. 3D laser scanners are commercially available (e.g., from Tiger Supplies Inc., Irvington N.J.; Laser Design and GKS Services, Minneapolis, Minn.; Riegl USA, Orlando, Fla. and Faro USA, Lake Mary, Fla.). In some embodiments, waveform LiDAR (e.g., available from Riegl, Orlando, Fla.) is utilized.

In some embodiments, high speed high density (HD) video is used to capture images of fruits and tree or vine features. The quality of video captured is important for accurate analysis. In some embodiments, video that is uncompressed 1080p at a speed of 60 frames a second or faster is utilized. In some embodiments, a fisheye lenses of 160° or greater is utilized.

Infrared thermography (IRT), thermal imaging, and thermal video are examples of infrared imaging science. Thermal imaging cameras detect radiation in the infrared range of the electromagnetic spectrum (roughly 9,000-14,000 nanometers or 9-14 µm) and produce images of that radiation, called thermograms. Since infrared radiation is emitted by all objects above absolute zero according to the black body radiation law, thermography makes it possible to see one's environment with or without visible illumination. The amount of radiation emitted by an object increases with temperature; therefore, thermography allows one to see variations in temperature. This is particularly useful when dealing with plant species that have very dense leaf coverage since the temperature differential between the leaf and the fruit are very different temperature profiles. High speed HD video hardware is commercially available (e.g., from NAC Image Technology, Simi Valley, Calif.; Olympus, Tokyo, Japan; Panasonic). Thermal imaging equipment is commercially available (e.g., from FLIR Systems, Boston, Mass. and L-3 Communications, New York, N.Y.).

In some embodiments, the capturing of this data utilizes specialized equipment mounted to vehicle (e.g., 4 wheel drive, flying vehicle, or off road vehicle). Any manned or unmanned vehicle that drives on the ground or flies low to the ground (e.g., unmanned or manned aircraft) may be utilized to transport the mapping hardware throughout the area to be surveyed. In some embodiments, a single data collection unit is capable of scanning two acres or more (e.g., 5, 10, 12, 15 or more) per hour in terrestrial applications.

In some embodiments, the present invention provides data analysis software and computer hardware configured to analyze data from the GPS, scanners and video cameras described herein. In some embodiments, analysis systems include user interfaces and display systems. For example, the 3D scanner creates a point cloud which is a set of vertices in a three-dimensional coordinate system. These vertices are usually defined by X, Y, and Z coordinates, and is typically intended to be representative of the external surface of an object. In some embodiments, point clouds of trees and vines are collected to determine the height of the plant, the trunk diameter, and the leaf density, all of which are determinants of health and productivity and each of these is derived as part of an automated process called classification. The classified data is then loaded, another automated process, into the database for access by the end user.

In some embodiments, software analyzes imaging data on a per tree or per vine basis. In some embodiments, data collected for a particular tree or orchard is inserted into a relational database providing connectivity to other industry standard software products. In some embodiments, software performs one or more (e.g., all) of the following functions: a) assembly of point cloud; b) correlation of data to map coordinates; c) refining of video data; and d) geo-registration of point cloud and video data. In some embodiments, the following information is provided to an end user: tree trunk diameter, height of tree, volume of tree, leaf density of tree, color of leaves on tree, GPS location of tree, bar code data for tree, number of blossoms on tree, and an annotated or un-annotated photograph of the tree (see e.g., FIG. 1).

In some embodiments, the present invention provides methods of analyzing fruit free quality and growth (e.g., including but not limited to, counting blossoms or fruit on the tree or vine (green or ripe), geo-locating plant or trees, determining age and health of tree or vine based on trunk diameter, leaf density, leaf color and overall volume). The methods find use in a variety of research and commercial applications in the agricultural, finance, banking, commodities, property appraisal, and insurance industry.

In some embodiments, crop data is utilized to a allow user to predict crop harvest by counting hanging fruit and measuring trunk diameter, leaf density, leaf color and overall volume. This is accomplished by utilizing a process that collects data in three formats: point cloud via 3D laser scanning; geo-location data via survey grade GPS; and photographic data via High speed HD video and/or thermal imaging.

In some embodiments, the systems and methods described herein find use in identifying subspecies of a particular species of tree or vine. In some embodiments, the systems and methods described herein find use in detecting disease (e.g., through the addition of multispectral and/or hyperspectral sensors). Hyperspectral imaging works by the development of a digital fingerprint. Unlike a conventional digital camera, which has three bands (red, green, blue) multispectral and hyperspectral imaging use more bands. In the case of multispectral dozens and hundreds for hyperspectral. For example, there are approximately 250 species of pecans in the US and the pecan tree has a particular signature in the electromagnetic spectrum and each of those sub-species have related but unique signature. In the case of Disease such as "citrus greening", "blight" or "citrus canker" specific conditions are manifested in the leaf, trunk and/or fruit that change the spectral signature making them identifiable through machine vision techniques. Additional details are described, for example, in Lan et al., Applied Engineering in Agriculture Vol. 25(4): 607-615 and Kumar et al., 2010; each of which is herein incorporated by reference in its entirety.

In some embodiments, identification of subspecies or disease is performed simultaneously with the other data that is being collected (LiDAR, photos, etc.) and geo-registered via GPS along with the other data.

In some embodiments, the data collected using the systems and methods described herein finds use in guiding sprayers through real-time mapping or premapping (e.g., commercial sprayers). Spraying represents a very large part of the budget of a grower and using the right kind of spray (herbicide, pesticide, and/or nutrient), in the proper amount, at the right time can have a dramatic impact on the farmers profitability. In some embodiments, data is collected using the systems and methods described herein (e.g., trunk centroid, tree height, canopy density, canopy diameter, species of tree, longitude and latitude) are used to control the sprayers. This data (e.g., in csv format) tells the sprayer as it travels through the grove from precalculated data, on a per tree bases, when to spray, how long to spray, and what chemicals to spray.

In some embodiments, the present invention provides computer implemented systems and methods for performing fruit tree analysis and displaying the results to a user. In some embodiments, computer implemented systems and methods generate a report of the results of the analysis methods that provide information (e.g., fruit yield, tree quality, harvest date predictions, sprayer coordinates) to a user. In some embodiments, the report is provided over the Internet (e.g., on a smart phone, tablet or other wireless communication device) or on a computer monitor.

In some embodiments, the systems and methods of the present invention are provided as an application service provider (ASP) (e.g., can be accessed by users within a web-based platform via a web browser across the Internet; is bundled into a network-type appliance and run within an institution or an intranet; or is provided as a software package and used as a stand-alone system on a single computer).

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

I claim:

1. A plant analysis system, comprising:
   a) a data acquisition component comprising a 3D laser scanner, a camera, and a survey grade global positioning satellite ("GPS") receiver,
      wherein said survey grade GPS receiver is configured to measure a location of said data acquisition component with a sub centimeter level of accuracy,
      wherein said 3D laser scanner is configured to measure the distance between said data acquisition component and a plant utilizing waveform light detection and ranging ("LiDAR"), and to assemble point cloud data, by creating a plurality of three dimensional vertices, wherein each vertex represents where said plant was located relative to said 3D laser scanner, and wherein said plurality of three dimensional vertices as a whole represents the external surface of an object on said plant,
      wherein said camera is configured to collect photographic data by taking an image of said plant,
   b) a transport component configured to transport said data acquisition component to collect data on said plant; and
   c) a processor configured to:
      geo-register the point cloud data and photographic data using said location of said data acquisition component, wherein said point cloud data is geo-registered by translating said relative three dimensional coordinates of each vertex measured by said 3D laser scanner into GPS coordinates such that each three dimensional vertex of said assembled point cloud data is associated with a GPS coordinate and wherein said photographic data is geo-registered by associating each three dimensional vertex of said assembled point cloud data with a pixel of said photographic data, and wherein each three dimensional vertex of said assembled point cloud data is associated with said GPS coordinates and said pixel of said photographic data using a relational database,
      determine plant color based on said photographic data,
      generate classification data comprising plant stem diameter, plant height, plant volume, and plant leaf density, using said GPS coordinates of said assembled point cloud data and said plant color,
      determine quality of said plant based on said plant stem diameter, said plant height, said plant volume, said plant leaf density, and together with said plant color, and
      spray said plant, using a fruit tree sprayer, based on said quality of said plant, wherein said fruit tree sprayer controls when to spray, how long to spray, and what chemicals to spray on said plant based on said quality of said plant.

2. The system of claim 1, wherein said camera further comprises a thermal video camera configured to collect thermal data and said quality of said plant is further determined based on said thermal data.

3. The system of claim 2, wherein said data acquisition component further comprises a multispectral or hyperspectral sensor for gathering spectral data, and wherein said quality of said plant is further based on said spectral data.

4. The system of claim 1, wherein said processor is further configured to generate an annotated photograph of said plant.

5. The system of claim 1, wherein said plant is a fruit tree, bush, or vine selected from the group consisting of abiu, acerola, almond, amla (indian gooseberry), apple, apricot, aprium, artichokes, avocados, bael, bananas, ber (indian plum), blackberries, blood orange, blueberries, breadfruit, calamondin, cantaloupe melon, carambola (starfruit), cashew, the fruit, cherries, chestnut, chocolate, chokecherry, citron, coconuts, coffee, corn plant, crabapple, cumaquat, currant, custard-apple, dates, dewberries, dragon fruit, durian, feijoa, fig, grapefruit, grapes, guava, hazelnut, honeydew, hops, jaboticaba, jackfruit, jujube, kaffir lime, key lime, kiwifruit, kumquat, lemons, limes, loganberries, longan, loquat, lychee, mandarin, mangoes, mangosteen, medlar, morello cherry, mulberries, natal plum, nectarines, olives, oranges, papayas, passion fruit, pawpaw, peaches, pears, pecans, persimmon, pineapples, plums, pluot, pomegranate, pomelo, prune, pummel, pumpkin, raspberries, red banana, rock melon, sabine, sapodilla (chikoo), sapote, soursop, starfruit, stone fruit, strawberries, strawberry tree, sugar-apple (sharifa), surinam cherry, tamarillo, tamarind, tangelos, tangerines, tomatoes, ugli, uglifruit/uniqfruit, walnut, watermelon, a grape vine, a tomato vine, a corn plant and an apple tree.

6. The system of claim 5, wherein said fruit tree is selected from the group consisting of orange, grapefruit, mandarin, tangerine, pomelo, lemon, lime, key lime, citron, kumquat, tangelo, ugli, and blood orange.

7. The system of claim 1, wherein said processor further comprises a user interface configured to display said point cloud data, said photographic data, and said quality of said plant.

8. The system of claim 1, wherein said processor is further configured to predicted fruit yield of said plant, said predicted fruit yield determined by identifying a number of fruits on said plant based on said assembled point cloud data and said plant color.

9. A method, comprising:
   a) transporting a data acquisition component, wherein said data acquisition component comprises a 3D laser scanner, a camera, and a survey grade global positioning satellite ("GPS") receiver, b) collecting waveform light detection and ranging ("LiDAR") data on a plant using said 3D laser scanner while said data acquisition component is being transported by said transport component wherein said 3D laser scanner is configured to measure the distance between said data acquisition component and said plant and assemble point cloud data by creating a plurality of three dimensional vertices, wherein each vertex represents where said plant was located relative to said 3D laser scanner, and wherein said plurality of three dimensional vertices as a whole represents the external surface of an object on said plant;

c) collecting photographic data by taking an image of said plant using said camera;

d) measuring a location of said data acquisition component using said survey grade GPS receiver, wherein said survey grade GPS receiver is configured to measure location with a sub centimeter level of accuracy;

e) geo-registering said point cloud data and photographic data, wherein said point cloud data is geo-registered by translating said relative three dimensional coordinates of each vertex measured by said 3D laser scanner into GPS coordinates such that each three dimensional vertex of said assembled point cloud data is associated with a GPS coordinate and wherein said photographic data is geo-registered by associating each three dimensional vertex of said assembled point cloud data with a pixel of said photographic data, wherein each three dimensional vertex of said assembled point cloud data is associated with said GPS coordinates and said pixel of said photographic data using a relational database;

f) determining plant color based on said photographic data;

g) determining classification data comprising plant stem diameter, plant height, plant volume, and plant leaf density using said GPS coordinates of said assembled point cloud data;

h) determining quality of said plant analyzing based on said plant stem diameter, said plant height, said plant volume, said plant leaf density, and together with said plant color, and i) spraying said plant, using a fruit tree sprayer, based on said quality of said plant, wherein said fruit tree sprayer controls when to spray, how long to spray, and what chemicals to spray on said plant based on said quality of said plant.

10. The method of claim 9, wherein said data acquisition component further comprises a thermal imaging camera configured to collect thermal data and said quality of said plant is further determined based on said thermal data.

11. The method of claim 9, wherein said quality of said plant is based on a number of blossoms counted on said plant, wherein the number of blossoms are determined by said geo-registered vertices of said assembled point cloud data.

12. The method of claim 9, wherein said plant is a fruit tree, bush, or vine selected from the group consisting of abiu, acerola, almond, amla (indian gooseberry), apple, apricot, aprium, avocados, artichokes, bael, bananas, ber (indian plum), blackberries, blood orange, blueberries, breadfruit, calamondin, cantaloupe melon, carambola (starfruit), cashew, the fruit, cherries, chestnut, chocolate, chokecherry, citron, coconuts, coffee, corn plant, crabapple, cumaquat, currant, custard-apple, dates, dewberries, dragon fruit, durian, feijoa, fig, grapefruit, grapes, guava, hazelnut, honeydew, hops, jaboticaba, jackfruit, jujube, kaffir lime, key lime, kiwifruit, kumquat, lemons, limes, loganberries, longan, loquat, lychee, mandarin, mangoes, mangosteen, medlar, morello cherry, mulberries, natal plum, nectarines, olives, oranges, papayas, passion fruit, pawpaw, peaches, pears, pecans, persimmon, pineapples, plums, pluot, pomegranate, pomelo, prune, pummel, pumpkin, raspberries, red banana, rock melon, sabinc, sapodilla (chikoo), sapotc, soursop, starfruit, stone fruit, strawberries, strawberry tree, sugar-apple (sharifa), surinam cherry, tamarillo, tamarind, tangelos, tangerines, tomatoes, ugh, uglifruit/uniqfruit, walnut, watermelon, a grape vine, a tomato vine, and a corn plant.

13. The method of claim 12, wherein said fruit tree is selected from the group consisting of orange, grapefruit, mandarin, tangerine, pomelo, lemon, lime, key lime, citron, kumquat, tangelo, ugh, and blood orange.

14. The method of claim 9, wherein said processor further comprises a data storage, and a user interface configured to display said point cloud data.

15. The method of claim 9, further comprising determining plant health or predicted fruit ripening period, wherein said plant health or predicted fruit ripening period are determined by said geo-registered vertices of said assembled point cloud data.

16. The method of claim 9, further comprising the step of using said analyzed data to control fruit tree sprayers based on a species of said plant.

17. The method of claim 16, wherein said guiding fruit tree sprayers comprises an action selected from the group consisting of when to spray, how long to spray, and what chemicals to spray.

18. The method of claim 9, wherein said method further comprises the steps of:
    gathering spectral data for said plant by a multispectral or hyperspectral sensor; and
    identifying species or subspecies of said plant based on said assembled point cloud data and said spectral data,
    wherein the identification of species or subspecies is performed simultaneously with the collection and geo-registration of the LiDAR data.

19. The method of claim 18, wherein said method further comprises the step of identifying a disease in said plant or a fruit on said plant, said disease manifested in a leaf, a stem, or said fruit of said plant, wherein said disease is detected by correlating said spectral data gathered for said plant with a spectral signature of a diseased plant or diseased fruit.

20. The method of claim 19 wherein said disease is citrus greening, blight, or citrus canker.

21. The system of claim 9 further comprising identifying a unique radio frequency identifier ("RFID") code associated with a plant.

* * * * *